(12) United States Patent
Dunker et al.

(10) Patent No.: US 7,662,108 B2
(45) Date of Patent: Feb. 16, 2010

(54) BIOPSY HOLDER FOR A BIOPSY CANNULA

(75) Inventors: Thomas Dunker, Teltow (DE); Dirk Hornscheidt, Berlin (DE); Frank Kniep, Grossbeeren/OT Kleinbeeren (DE); Suhail Rishmawi, Berlin (DE)

(73) Assignee: SOMATEX Medical Technologies GmbH, Teltow (DE)

( * ) Notice: Subject to any disclaimer, the term of this patent is extended or adjusted under 35 U.S.C. 154(b) by 383 days.

(21) Appl. No.: 10/532,518

(22) PCT Filed: Oct. 23, 2003

(86) PCT No.: PCT/EP03/11727

§ 371 (c)(1),
(2), (4) Date: Apr. 25, 2005

(87) PCT Pub. No.: WO2004/037093

PCT Pub. Date: May 6, 2004

(65) Prior Publication Data

US 2006/0052721 A1 Mar. 9, 2006

(30) Foreign Application Priority Data

Oct. 25, 2002 (DE) .............................. 102 50 071
May 20, 2003 (EP) .............................. 03011430

(51) Int. Cl.
*A61B 10/00* (2006.01)
(52) U.S. Cl. ..................................... 600/567
(58) Field of Classification Search ............... 600/567, 600/562, 564
See application file for complete search history.

(56) References Cited

U.S. PATENT DOCUMENTS

| | | | |
|---|---|---|---|
| 4,461,305 A | | 7/1984 | Cibley |
| 4,781,202 A | * | 11/1988 | Janese ......................... 600/567 |
| 4,926,877 A | * | 5/1990 | Bookwalter .................. 600/567 |
| 5,059,197 A | * | 10/1991 | Urie et al. .................... 606/116 |
| 5,257,632 A | * | 11/1993 | Turkel et al. ................. 600/567 |
| 5,333,619 A | * | 8/1994 | Burgio ......................... 600/567 |
| 5,385,151 A | * | 1/1995 | Scarfone et al. ............. 600/567 |
| 5,462,062 A | * | 10/1995 | Rubinstein et al. .......... 600/567 |
| 5,885,226 A | * | 3/1999 | Rubinstein et al. .......... 600/564 |
| 5,910,121 A | * | 6/1999 | Paolo et al. .................. 600/562 |
| 6,080,115 A | * | 6/2000 | Rubinstein ................... 600/567 |
| 6,322,581 B1 | * | 11/2001 | Fukuda et al. ............... 606/223 |
| 6,416,484 B1 | * | 7/2002 | Miller et al. ................. 600/564 |
| 6,443,910 B1 | | 9/2002 | Clark et al. |
| 6,827,692 B2 | * | 12/2004 | Castellacci .................. 600/567 |

FOREIGN PATENT DOCUMENTS

EP          43 05 226          9/1993

OTHER PUBLICATIONS

International Search Report, PCT/EP03/11727 Jan. 4, 2004.

* cited by examiner

*Primary Examiner*—Max Hindenburg
*Assistant Examiner*—Michael C Stout
(74) *Attorney, Agent, or Firm*—Collard & Roe, P.C.

(57) ABSTRACT

A biopsy holding device for a biopsy cannula to perform transcutaneous biopsies, in particular of hard tissue and bone marrow tissue, uses a wire that can be inserted into the proximal end of a biopsy cannula and can be pushed in between the inner wall of the biopsy cannula and the tissue-removing biopsy cylinder.

10 Claims, 5 Drawing Sheets

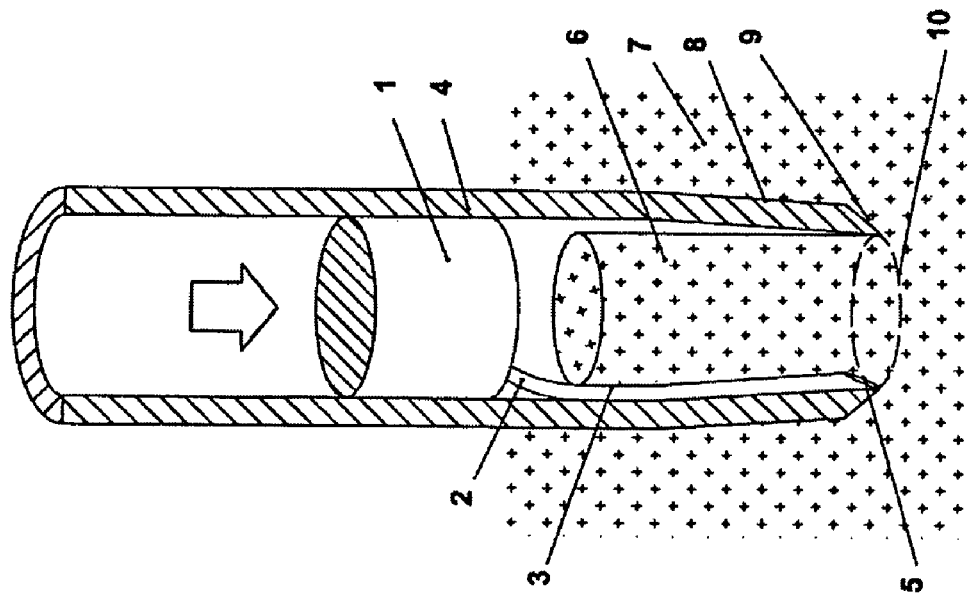
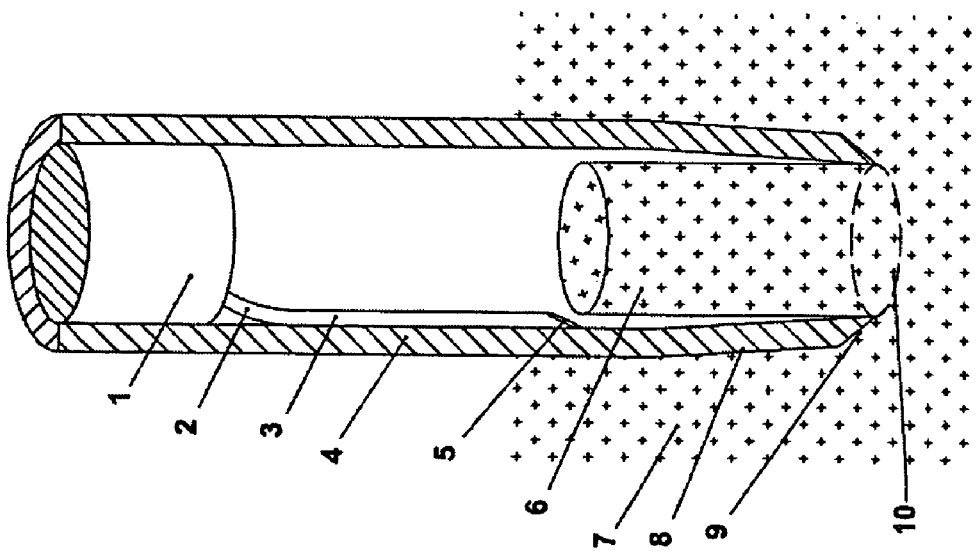

BIOPSY HOLDER FOR A BIOPSY CANNULA

CROSS REFERENCE TO RELATED APPLICATIONS

Applicants claim priority under 35 U.S.C. §119 of German Application No. 102 50 071.1 filed Oct. 25, 2002 and European Application No. 03011430.0 filed May 20, 2003. Applicants also claims priority under 35 U.S.C. §365 of PCT/EP2003/011727 filed Oct. 23, 2003. The international application under PCT article 21(2) was not published in English.

BACKGROUND OF THE INVENTION

1. Field of the Invention

The invention relates to a biopsate holding device for a biopsy cannula to perform transcutaneous biopsies, in particular of hard tissue and bone marrow tissue, by means of a biopsate holding device that can be inserted into the proximal end of a biopsy cannula and pushed in between the inner wall of the biopsy cannula and the tissue-removing cylinder.

2. Description of the Related Art

The state of the art can be described as follows: Conventional needles for biopsic, transcutaneous removal of hard tissue, in particular bone marrow tissue, consist of a cylinder of different lengths and diameters, whose proximal end is fitted with a grip and whose distal end is tapered and narrows into a boring with a cutting edge. Is the needle pressed into the tissue and simultaneously rotated around its axis it cuts a cylindrical piece out of the tissue to be removed that is taken up in the hollow interior of the needle. Withdrawal of the cylinder from the tissues as biopsy requires the subsequent interruption of the connection of the distal cylinder end with the remaining tissues into which the needle has been inserted. For this purpose, in conventional methods the grip of the needle is set into vibrations that run in a plane at a right angle to the needle axis with a trocar being provided at the point of insertion into the tissue. As a result of this approach, the connections between the distal end of the biopsy and the remaining tissue are broken at the distal end of the needle that can be withdrawn and whose interior contains the biopsy material that is detained by the tapered end of the needle. This method of examination has the following disadvantages: Frequently the biopsy material is not retained in the needle since it is not completely loosened from the remaining tissue and since there is an, albeit low, negative pressure generated in the needle while it is being pulled out of the tissue so that the biopsy material is subsequently drawn in although this suction cannot overcome the opposite brake effect that is caused by the tapering of the needle end. All this makes the repetition of the entire biopsy examination necessary. Frequently the explained difficulties while the needle is pulled out cause the biopsy material to slip out of the distal end of the needle which may result in an injury and a rupture of the biopsy cylinder during the withdrawal through the tissue and a loss of parts of the distal portion of the biopsy. The movements or vibrations that are exerted onto the needle in order to separate the biopsy often cause smaller fractures at the surface and interruptions in the coherence of the hard tissue into which the needle was inserted, with this possibility being increased with the distance from the tissue surface. The results are in for the patient and damaging of the needle that is prone to become bent and thus lose its necessary straightness.

Known is also a patent DE 43 05 226 "Device for needles for transcutaneous biopsies" that describes an accessory device for conventional biopsy needles for transcutaneous tissue biopsy, in particular hard tissue and bone marrow tissue. The accessory device permits the trouble-free performance of biopsies at any tissue, from hard, compact bones to very thin and brittle bone marrow tissue, without the danger that the biopsy needle is withdrawn without a tissue sample. The accessory device reduces the danger of damaging tissues during a biopsy and mitigates pain in patients. The basic principle of the accessory device is that an insertion structure is inserted at the proximal end of the biopsy needle and pushes itself between the inner wall of the needle and the tissue cylinder. The cylindrical configuration of the biopsy cannula makes sure that this structure is clamped together to retain the biopsate. The disadvantage of this technical solution lies in the fact that the clamping of the structure subjects the retained biopsate to a press fit. This press fit causes crush artefacts of the biopsate. The conclusion is that the crush artefacts may distort the results of the subsequent examination of the biopsate.

SUMMARY OF THE INVENTION

Basis of this invention is the problem of finding a biopsate holding device for a biopsy cannula to perform transcutaneous biopsies of tissue, in particular hard tissue and bone marrow tissue, and overcome the disadvantage of the state of the art and make sure that biopsate removal via the biopsy cannula becomes possible with very few crush artefacts and thus ensure the guaranteed biopsate removal via the biopsy cannula.

According to invention the problem is solved by realising a biopsate holding device for a biopsy cannula for the performance of transcutaneous biopsies of tissue, in particular hard tissue and bone marrow tissue, with patent claim 1 and its sub-claims being executed as the technical solution.

The biopsate holding device is executed in the form of a grip end and a wire attached to the grip end. The grip end can be arrested to the grip end of the biopsy cannula. The distal end of the wire is provided with a connection that makes sure that the wire is present at the distal end of the biopsy cannula at the inner wall of the biopsy cannula and a biopsate cylinder. The wire with a pre-stress angle is arranged at the center of the grip end, the wire being bent in a bending direction with a pre-stress angle between 1° and 90°. The wire and the provided tip with a bevelling should reasonably have a bevelling angle of 5° to 85°, preferably 20°. The wire with bevelling is executed so that the bevelling is directed towards the biopsate cylinder to be removed. The bevelling can also be executed as a hollow or bulged grind. What is essential is that the wire has a sufficient length for the removal of biopsate from the biopsy cannula. The wire extends to the end of the biopsy cannula.

This invention also provides a solution in which a shank is arranged at the grip end. The shank is inserted via the grip end into the biopsy cannula at the proximal end of the biopsy cannula. A wire with a defined pre-stress angle is fitted to the distal end of this shank. The shank for proximal insertion into the biopsy cannula has a grip end that can be arrested to the grip end of the biopsy cannula after insertion into the biopsy cannula. The wire at the distal end of the shank is arranged in a fixed connection with a pre-stress angle between 1° and 90° to tolerate each application. The distal end of the wire has a tip with bevelling, with the bevelling also being executed according to the application from 5° to 85°, preferably 20°, and the bevelling being directed towards the biopsy cylinder of the biopsate to be removed. The length of the shank and the pertaining wire is defined such that the wire length is preferably ca. 25 mm. The ratio of the dimensions must be kept in such a manner that the shank upon its insertion into the biopsy cannula of a known design has such a length that it ends directly at the end of the biopsy cannula between the inner wall of the biopsy cannula and the biopsate. Hence, it must be ensured that the biopsy cannula with its distal end forms a unit with the distal end of the shank wire. The wire that is fixed to the shank preferably has a roughened surface. The wire profile can be variably shaped. The cross-section of the wire is designed in such a manner that only minimal crush artefacts occur between the inner wall of the biopsy cannula and the interior biopsate cylinder when the shank is fixed in the biopsy cannula. The wire diameter is preferably ca. 0.35 mm.

The shank described therein with a wire at its distal end for insertion at the proximal end into a known biopsy cannula permits the trouble-free performance of a biopsy at any tissue, from hard, compacts bones to very thin and brittle bone marrow tissue, without the danger that the biopsy cannula is removed without a tissue sample. Arrangement of the shank with the wire at its distal end reduces the danger of damaging tissues during a biopsy and mitigates pain in patients. Finally, also the mechanical stress on the biopsy cannula is reduced since deflections are avoided which will extend the service life of the biopsy cannula. It is also ensured that biopsate is taken in a high quality since only minor crush artefacts occur between the inner wall of the biopsy cannula and the biopsate cylinder. Thus a highly reliable analysis of the biopsate is possible due to the low level of crush artefacts.

BRIEF DESCRIPTION OF THE DRAWINGS

Further advantages and features of the invention are described in the claims and the following practical example in which a shank for a biopsy cannula according to invention is explained in detail with drawing references. The practical example is illustrated by the following figures:

FIG. 4: Placing the biopsy needle in the biopsate
FIG. 5: Placing the shank in the biopsy needle

DETAILED DESCRIPTION OF PREFERRED EMBODIMENTS

Figure 1A:
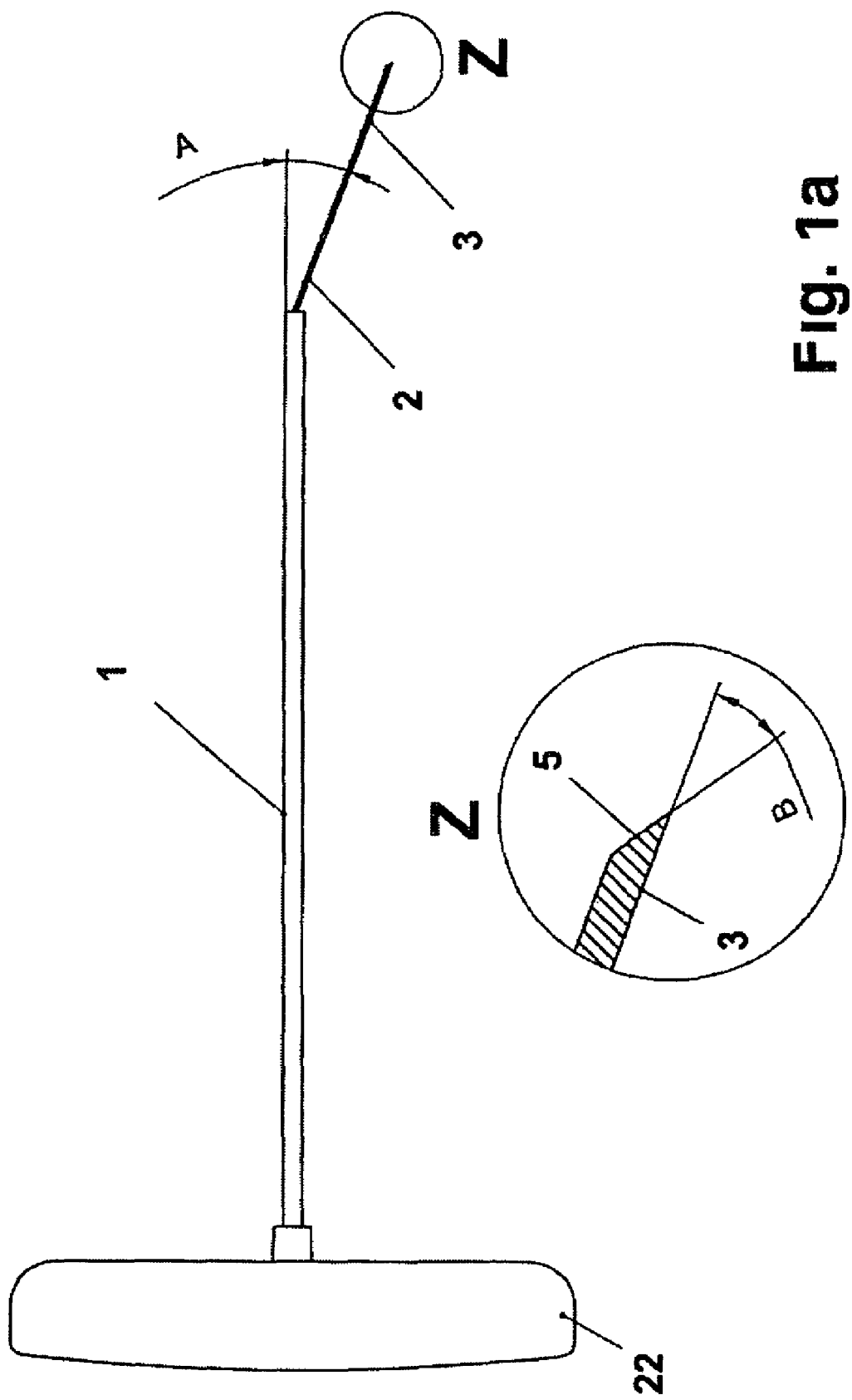
FIG. 1*a*: Shank with grip end
Figure 1B:
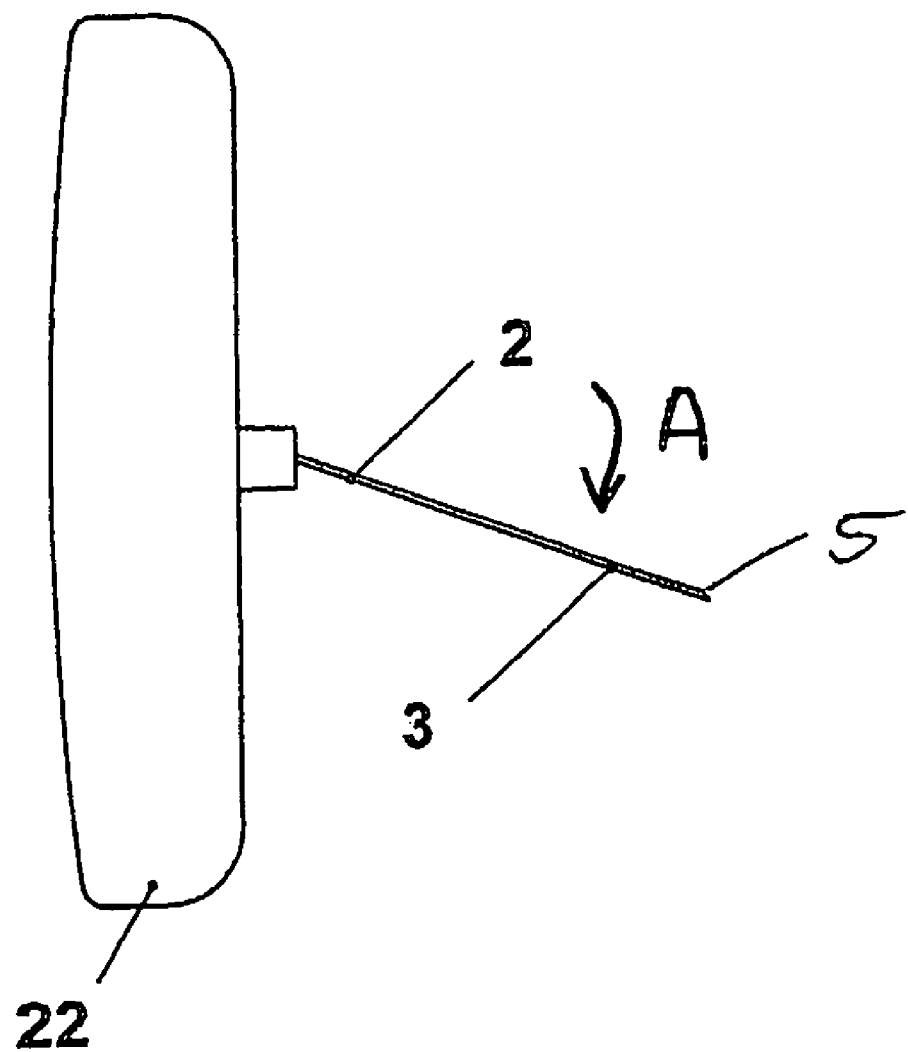
FIG. 1*b*: Wire with grip end

FIG. 1*b* shows a device according to invention in which a grip end 20 is fitted with an arrestable grip end 22. A wire 3 bent in a bending direction A at a pre-stress angle 2 is attached at the center of grip end 22. The length of the wire 3 is executed so that essentially the immediate end of the biopsy cannula 4 is reached. The pre-stress angle 2 ensures the gliding of the wire 3 along the inner wall of the biopsy cannula 4 between the biopsate cylinder 6. The bevelling 5 of the wire 3 is executed so that the bevelling 5 is directed towards the biopsate cylinder 6 and thus an optimal displacement of the biopsate cylinder 6 is facilitated upon insertion of the wire 3 between the inner wall of the biopsy cannula 4 and the biopsate cylinder 6. Basically it can be assumed that the length of the wire will always correspond to the length of the respective biopsy cannula 4. Should the biopsy cannula 4 have a size that makes a correct insertion of the wire 3 via the grip end 22 no longer possible the following FIG. 1*a* with an additionally mounted shank 1 is executed.

Figure 2:
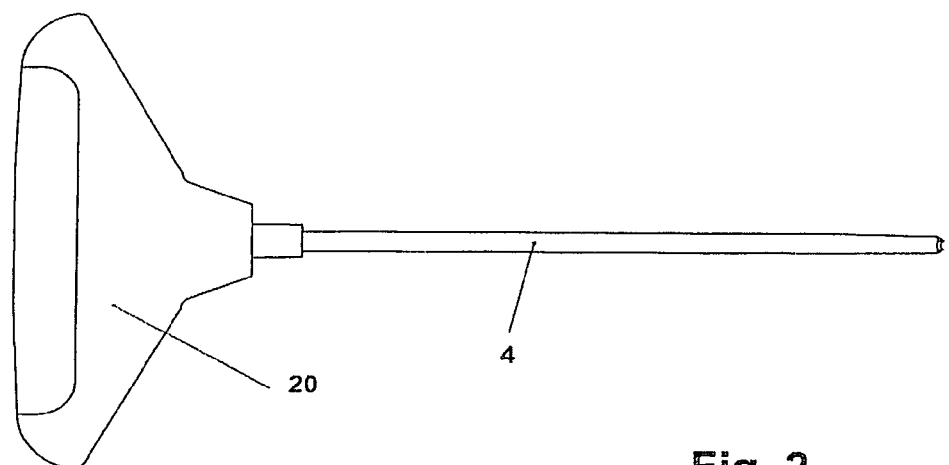
FIG. 2: Biopsy needle

FIG. 1*a* shows a shank 1 with a grip end 22 at its proximal end and a wire 3 with an appropriate pre-stress angle 2 at its distal end. The shank 1 is arranged so that it can be inserted conveniently into the biopsy cannula 4 as shown in FIG. 2. It is important to mention that the grip 22 of the shank 1 is executed so that it can firmly arrested into the grip 20 of the biopsy cannula 4 after insertion of the shank 1. A wire 3 with a length of 25 mm is provided at the distal end of the shank 1. The wire 3 has a tip with a bevelling 5 with the angle of bevelling B being executed between 5° and 85°, the bevelling B is preferably ca. 20° in the practical example. The bevelling 5 is arranged so that it is directed towards the biopsate cylinder 6 upon insertion of the shank 1 into the biopsy cannula 4 between the biopsate cylinder 6 and the inner wall of the biopsy cannula 4. The pre-stress angle 2 that defines the arrangement of the wire 3 is between 1° and 90°. In the preferred practical example the pre-stress angle 2 is ca. 10°. This pre-stress angle 2 is attained by the respective arrangement of the wire 3 at the distal end of the shank 1 by means of a specific mode of attachment. The arrangement of the pre-stress angle 2 of the wire 3 causes at any rate a tension of the wire 3 upon insertion of the shank 1 into a biopsy cannula 4 as shown in FIG. 2. The wire 3 of the shank 1 is pushed into the biopsy cannula 4 with this pre-tension when inserted at the outmost edge between the inner wall of the biopsy cannula 4 and the interior biopsate cylinder 6. Thus it is ensured that a very small number of biopsate artefacts occur when the biopsate is removed via the biopsy cannula 4.

Figure 3:
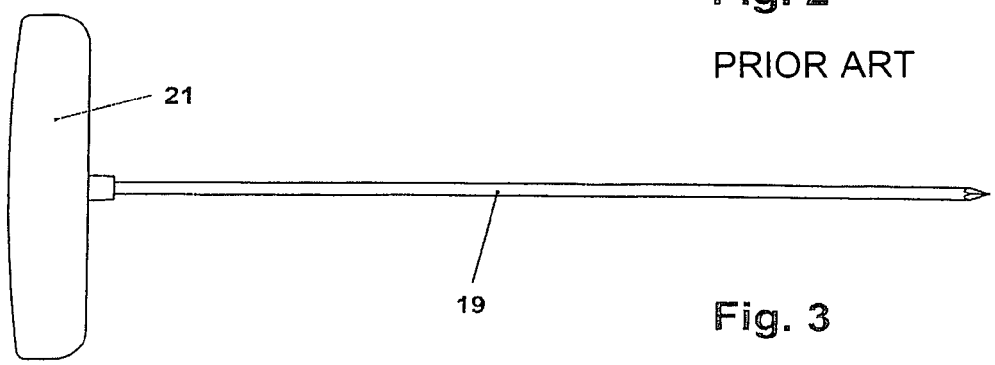
FIG. 3: Trocar

FIGS. 2 and 3 show a known biopsy cannula 4 and a trocar 19 used for placing the biopsy cannula 4. The grip ends 21 of the trocar 19 and 22 of the shank 1 can be positioned and firmly arrested in the grip end 20 of the biopsy cannula 4. The biopsy cannula 4 in FIG. 2 is placed via the trocar 19 in FIG. 3 into the tissue to be removed.

Placing of the biopsy cannula 4 in the described manner ensures that a cylindrical biopsate 6 is placed in the interior of the biopsy cannula 4 in the distal end of the biopsy cannula 4. This placing of the biopsy cannula 4 is depicted in FIG. 4. After the biopsy cannula 4 has been placed into the tissue to be taken and the interior biopsy cylinder 6, the shank 1 is inserted proximally into the biopsy cannula 4 via the grip 22 with the wire 3 at its distal end.

Placing of the shank 1 with the wire 3 at its distal end is shown graphically in FIG. 5 from setting the shank 1 to arresting the grip 22 of the shank 1 into the grip 20 of the biopsy cannula 4. The given pre-stress angle 2 and the resulting tension of the wire 3 drive the wire 3 by insertion of the shank 1 into the biopsy cannula 4 directly immediately at the inner wall of the biopsy cannula 4 between the inner wall and the biopsate cylinder 6. The cylindrical design of the biopsy cannula 4 at the distal end provides for a guiding tension of the wire 3. The length of the shank 1 with the wire 3 at its distal end is chosen so that the tip 5 of the wire 3 ends directly at the distal end of the biopsy cannula 4 after insertion and arresting of the grip 22 of the shank 1 into the grip 20 of the biopsy cannula 4.

Figure 7:
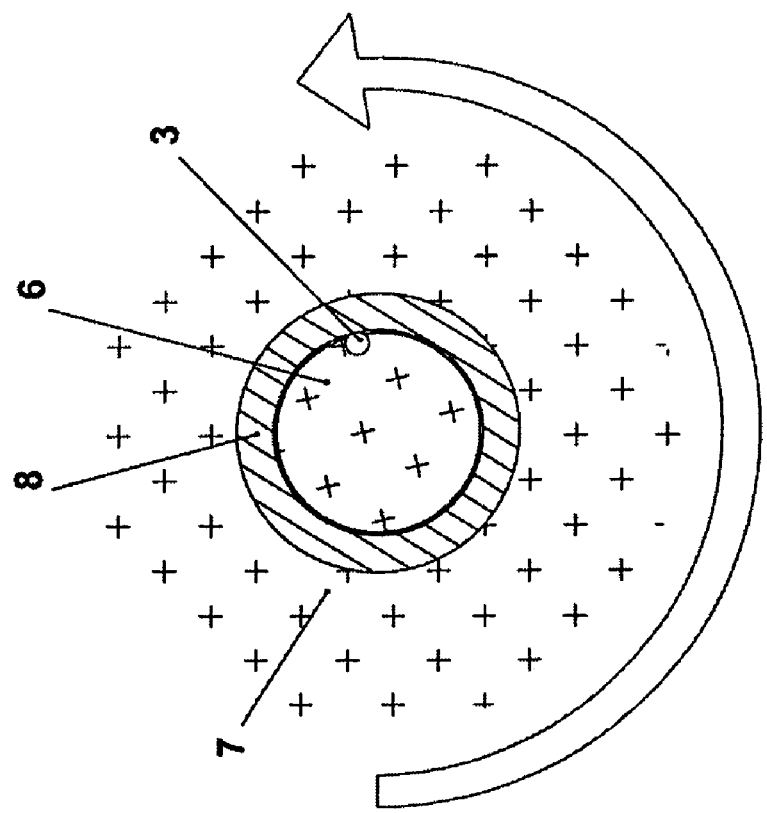
FIGS. 6 and 7: Views of the biopsy needle and needle 3 with the described rotary motion
Figure 6:
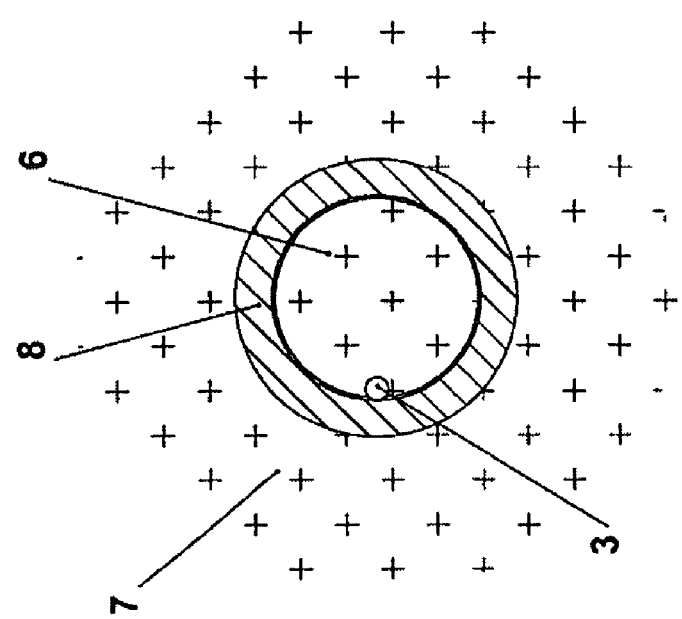

FIG. 6 and FIG. 7 show that the biopsy cannula 4 is subsequently handled such that a biopsate is shorn off by rotating the biopsy cannula 4. Following the rotation of the biopsy cannula 4 with the interior shank 1 the biopsy cannula is withdrawn from the tissue to be removed and the biopsate is taken out of an additional ejector after the shank 1 has been detached. A high quality for the further examination of the biopsate is ensured by the very low level of crush artefacture of the biopsate between the inner wall of the biopsy cannula 4 and the wire 3 of the shank 1 as well as the interior biopsy cylinder 6. The essential advantage of the shank 1 according to invention with the wire 3 at its distal end is that the penetration of the wire 3 of the shank 1 along the inner wall between the inner wall and the biopsate cylinder 6 generates a pressure which ensures that the biopsate cylinder 6 is retained at the distal end of the biopsy cannula 4 after rotation of the biopsy cannula 4 and thus provides a high guarantee that a biopsate is contained upon removal of the biopsy cannula 4.

REFERENCE CHARACTERS

1 Shank
2 Pre-stress angle
3 Wire
4 Biopsy cannula
5 Tip with a bevelling
6 Biopsate cylinder
7 Bone marrow
8 Tapering
9 Cutting edge of the cannula
10 Proximal connection surface
19 Trocar
20 Grip end
21 Grip end
22 Grip end of shank 1
B Bevelling angle

The invention claimed is:

1. A biopsy material holding device for a biopsy cannula insertable into a proximal end of the biopsy cannula and between an inner wall of the biopsy cannula and a tissue-removing cylinder to perform transcutaneous biopsies of tissues, said biopsy material holding device comprising a wire having a proximal end, a distal end and a wire tip at said distal end with bevelling arranged at the wire tip, said wire being bent in a bending direction at a pre-stress angle arranged at the proximal end of the wire, wherein the wire has a uniform round cross section between said pre-stress angle and said bevelling, said bevelling facing away from the bending direction, so that the wire including the wire tip glides along the inner wall of the biopsy cannula when inserted into the biopsy cannula.

2. The biopsy material holding device for a biopsy cannula according to claim 1 further comprising a grip end, wherein said wire is attached to said grip end.

3. The biopsy material holding device for a biopsy cannula according to claim 1 further comprising a grip end with an attached extension shank, said wire being fastened to the shank.

4. The biopsy material holding device for a biopsy cannula according to claim 1 wherein the wire tip has a bevelling angle B of 5° to 85°.

5. The biopsy material holding device for a biopsy cannula according to claim 1, wherein the bevelling of the wire is either hollow ground or bulged.

6. The biopsy material holding device for a biopsy cannula according to claim 2 wherein said wire is arranged at the center of the grip end, with the pre-stress angle being between 1° and 90°.

7. The biopsy material holding device for a biopsy cannula according to claim 1 wherein the wire has a length so that the wire reaches the distal end of the biopsy cannula when inserted in the biopsy cannula.

8. The biopsy material holding device for a biopsy cannula according to claim 2 wherein the grip end can be locked into the proximal end of the biopsy cannula.

9. The biopsy material holding device for a biopsy cannula according to claim 3 wherein the wire is firmly connected to the distal end of the shank and said pre-stress angle is between 1° and 90°, according to the specific application.

10. The biopsy material holding device for a biopsy cannula according to claim 3 wherein the grip end is lockable into the proximal end of the biopsy cannula and the length of the wire is 25 mm and ends at a direct end of the biopsy cannula after insertion of the shank and locking of the grip end into the proximal end of the biopsy cannula.

\* \* \* \* \*

UNITED STATES PATENT AND TRADEMARK OFFICE
CERTIFICATE OF CORRECTION

PATENT NO. : 7,662,108 B2
APPLICATION NO. : 10/532518
DATED : February 16, 2010
INVENTOR(S) : Dunker et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 478 days.

Signed and Sealed this

Thirtieth Day of November, 2010

David J. Kappos
*Director of the United States Patent and Trademark Office*